United States Patent [19]

Righter et al.

[11] Patent Number: 5,365,935

[45] Date of Patent: Nov. 22, 1994

[54] PORTABLE, MULTI-CHANNEL ECG DATA MONITOR/RECORDER

[75] Inventors: William H. Righter, Aloha; Andrew J. Nicoll, Hillsboro, both of Oreg.; Harold L. Kennedy, St. Louis, Mo.

[73] Assignee: Ralin, Inc., Bannockburn, Ill.

[21] Appl. No.: 90,298

[22] Filed: Jul. 12, 1993

Related U.S. Application Data

[60] Continuation-in-part of Ser. No. 983,798, Nov. 30, 1992, Pat. No. 5,226,425, which is a division of Ser. No. 757,254, Sep. 10, 1991, Pat. No. 5,191,891.

[51] Int. Cl.$^5$ .................................... A61B 5/0404
[52] U.S. Cl. ................................ 128/710; 128/696; 128/639
[58] Field of Search ............... 128/696, 699, 690, 710, 128/670, 904, 639, 640, 381, 384

[56] References Cited

U.S. PATENT DOCUMENTS

| | | | |
|---|---|---|---|
| 3,792,700 | 2/1974 | Sarnoff et al. | 128/639 |
| 3,799,148 | 3/1974 | Rowen | 128/704 |
| 3,819,863 | 6/1974 | Slaght | 128/904 |
| 3,872,252 | 3/1975 | Malchman et al. | 379/106 |
| 3,910,260 | 10/1975 | Sarnoff et al. | 128/639 |
| 3,934,267 | 1/1976 | Kosaka et al. | 128/711 |
| 3,938,507 | 2/1976 | Sarnoff et al. | 128/701 |
| 4,055,729 | 10/1977 | Vandling | 379/100 |
| 4,086,916 | 5/1978 | Freeman et al. | 128/661.07 |
| 4,120,294 | 10/1978 | Wolfe | 128/706 |
| 4,121,573 | 10/1978 | Crovella et al. | 128/640 |
| 4,129,125 | 12/1978 | Lester et al. | 128/671 |
| 4,173,971 | 11/1979 | Karz | 128/702 |
| 4,183,354 | 1/1980 | Sibley et al. | 128/711 |
| 4,221,223 | 9/1980 | Linden | 128/706 |
| 4,256,117 | 3/1981 | Perica et al. | 128/690 |
| 4,337,377 | 6/1982 | Van Riper et al. | 128/904 |
| 4,417,306 | 11/1983 | Citron et al. | 128/702 |
| 4,425,921 | 1/1984 | Fujisaki et al. | 128/690 |
| 4,489,731 | 12/1984 | Baumberg | 128/690 |
| 4,531,527 | 7/1985 | Reinhold, Jr. et al. | 128/696 |
| 4,535,782 | 8/1985 | Marangoni | 128/665 |
| 4,606,352 | 8/1986 | Geddes et al. | 128/702 |
| 4,622,979 | 11/1986 | Katchis et al. | 128/702 |
| 4,625,733 | 12/1986 | Saynajakangas | 128/687 |
| 4,633,881 | 1/1987 | Moore et al. | 128/659 |
| 4,679,144 | 7/1987 | Cox et al. | 128/702 |
| 4,802,008 | 1/1989 | Walling | 358/141 |
| 4,858,617 | 8/1989 | Sanders | 128/696 |
| 4,862,896 | 9/1989 | Reinhold, Jr. et al. | 128/696 |
| 4,883,064 | 11/1989 | Olson et al. | 128/696 |
| 4,889,134 | 12/1989 | Greenwold et al. | 128/696 |

(List continued on next page.)

FOREIGN PATENT DOCUMENTS

| | | | |
|---|---|---|---|
| 2514633 | 4/1983 | France | 128/696 |
| 2753165 | 11/1978 | Germany | 128/696 |

OTHER PUBLICATIONS

Tompkins, Willis J., "Patient Worn, Intelligent Arrythmia Systems," *IEEE Engineering In Medicine and Biology Magazine*, Dec. 1985, pp. 38–42.

(List continued on next page.)

*Primary Examiner*—George Manuel
*Attorney, Agent, or Firm*—Leydig, Voit & Mayer, Ltd.

[57] ABSTRACT

A portable apparatus having electronic circuitry for selectively monitoring and recording a user's electrocardiographic (ECG) data signals, wherein a first conductive electrode is disposed on a first surface of the apparatus casing for contact with an ECG lead position on the user's body and second and third paste-on electrodes are attached on the user's chest in positions which form the second and third electrodes in the standard Eindhoven triangle formation. A wristband is provided for securing the apparatus to the user's wrist and a microprocessor controls the electronic circuitry such that the user's ECG signal is monitored/recorded from six standard input channels. A modem device is attachable to the apparatus for effecting burst mode transmission of data to an external receiver.

32 Claims, 8 Drawing Sheets

U.S. PATENT DOCUMENTS

| | | |
|---|---|---|
| 4,928,690 | 5/1990 | Heilman et al. ............... 607/4 |
| 4,938,228 | 7/1990 | Righter et al. ............... 128/690 |
| 4,958,641 | 9/1990 | Digby et al. ............... 128/702 |
| 4,967,756 | 11/1990 | Hewitt ............... 128/680 |
| 4,974,607 | 12/1990 | Miwa ............... 128/904 |
| 4,991,200 | 2/1991 | Lin ............... 379/100 |
| 4,993,423 | 2/1991 | Stice ............... 128/696 |
| 5,012,814 | 5/1991 | Mills et al. ............... 128/697 |
| 5,029,590 | 7/1991 | Allain et al. ............... 128/710 |
| 5,036,852 | 8/1991 | Leishman ............... 128/904 |
| 5,041,918 | 8/1991 | Ishida et al. ............... 358/442 |
| 5,050,612 | 9/1991 | Matsumura ............... 128/670 |
| 5,217,020 | 6/1993 | Saltzstein et al. ............... 128/696 |

OTHER PUBLICATIONS

Instromedix HeartWatch (Brochure & Physician's Instruction Manual).
Sensocor R-Test.
Cardiocare MemoryTrace Monitor (Brochure, Patient Manual for Wrist Electrodes and Patient Manual for Skin Electrodes).
Survival Technology Inc. The CardioBeeper III Recorder.
Cardiotechnology, Inc. Cardioteam.
Cardiac Monitoring Innovations (CMI) Pat III.
Chidester, Bill, "Firm introduces new device to help hearts," *Hillsboro (Ore.) Argus*, Jan. 28, 1993.
Podolsky, Doug, "Your heart on display," *U.S. News & World Reports*, Oct. 1, 1990.
Ledger, Luc and Thivierge, Madeleine, "Heart Rate Monitors: Validity, Stability, and Functionality." *The Physician and Sports Medicine*, vol. 16, No. 5, May, 1988.
Polar Accurex Heart Rate Monitor.
Polar Cyclovantage Performance Monitor.
Polar Interface With Software.
Polar Optimex Heart Rate Monitor.
Polar Pacer Heart Rate Monitor.
Polar Target Heart Rate Monitor for Aerobics.
Polar Vantage Heart Rate Monitor.
Instromedix King of Hearts 300 Monitor.
Instromedix King of Hearts Express Monitor (Patients Instructions & Brochure).

| $M_1$ | $M_2$ | $M_3$ | $MUX_{80}OUT_+$ | $MUX_{82}OUT_-$ | LEAD CONFIGURATION |
|---|---|---|---|---|---|
| 0 | 0 | 0 | b | f | LI |
| 0 | 0 | 1 | d | f | LII |
| 0 | 1 | 0 | d | b | LIII |
| 0 | 1 | 1 | b | e | AVL |
| 1 | 0 | 0 | c | f | AVR |
| 1 | 0 | 1 | d | a | AVF |
| 1 | 1 | 0 | -- | -- | -- |
| 1 | 1 | 1 | -- | -- | -- |

PORTABLE, MULTI-CHANNEL ECG DATA MONITOR/RECORDER

CROSS REFERENCE TO RELATED APPLICATIONS

This application is a continuation-in-part of copending U.S. application Ser. No. 983,798, filed Nov. 30, 1992, now U.S. Pat. No. 5,267,425, which is a divisional of U.S. application Ser. No. 757,254, filed Sep. 10, 1991, U.S. Pat. No. 5,191,891, both entitled "Portable ECG Monitor/Recorder." The disclosures of these applications are hereby incorporated by reference.

FIELD OF THE INVENTION

The present invention relates to an apparatus for monitoring and recording electrocardiographic (ECG) data, and more particularly to a portable ECG data monitor/recorder capable of continuously recording ECG data from any of multiple data channels.

BACKGROUND OF THE INVENTION

Portable ECG data monitoring and recording devices for use by persons in out-patient (e.g., home or work) environments have long been known. Recently, compact devices have been developed that may be worn or carried by a user for monitoring and recording ECG data and transmitting the recorded data through a telephone handset to analyzing equipment at a doctor's office or centralized location. These devices each provide certain benefits, but also suffer from various shortcomings and deficiencies. These deficiencies relate primarily to either the physical size of the units or to the way in which the user is required to make contact with the electrodes and subsequently activate the recording sequence.

For example, with some of these known devices the user is required to apply the device (particularly its electrodes) to a body portion (e.g., bare chest) as soon as possible after the on-set of episodic symptoms, such as an arrhythmia. Of course, given the practical delays in finding the unit, locating a private place in which to effect the recording, opening or removing a chest-covering shirt or blouse, applying the unit to the chest and pushing the event button, transient episodic symptoms are often missed.

Other devices have attempted to overcome these "missed-event" deficiencies by requiring the user to apply two or more paste-on electrodes to their body, which electrodes are wired into the device. The unit is worn attached to the user's clothing and a memory loop feature is employed which allows the user ample time to activate the recording sequence after the on-set of episodic symptoms. Since the user actually wears attached electrodes, continuous monitoring is possible and the memory loop ensures that transient ECG data is rarely missed. Patients, however, are generally resistant to wearing a bulky device attached to their clothing, because the size and placement of the unit on the outside of clothing draws unwanted attention to the patient's medical condition. Moreover, due to the cumbersome nature of such continuous monitoring devices, the number and placement of electrodes is typically restricted. As a result, such devices are limited to obtaining ECG data readings from only one set of electrodes (i.e., from one channel).

SUMMARY OF THE INVENTION

In view of the foregoing, it is a primary object of the present invention to provide an apparatus that records medical-grade ECG data and yet is convenient and comfortable for a user to wear.

A related object of the present invention is to provide an ECG recorder that is capable of continuously recording ECG data from multiple data channels while minimizing the number of paste-on electrodes required.

Another object of the present invention is to provide a portable ECG recorder which operates so as to ensure long battery life.

A further object of the present invention is to provide a modem device for transmitting stored ECG data from the recorder to a receiving station.

Still another object of the present invention is to provide a portable ECG recorder which utilizes a limited number of slender and comfortable paste-on electrodes.

Yet another object of the present invention is to provide an ECG recorder which transfers data to a modem device in burst mode.

Other objects and advantages of the present invention will become apparent from the following detailed description when taken in conjunction with the drawings, in which:

While the invention will be described in connection with certain preferred embodiments, there is no intent to limit it to those embodiments. On the contrary, the intent is to cover all alternatives, modifications and equivalents included within the spirit and scope of the invention as defined by the appended claims.

DETAILED DESCRIPTION OF THE PREFERRED EMBODIMENTS

Figure 1A:
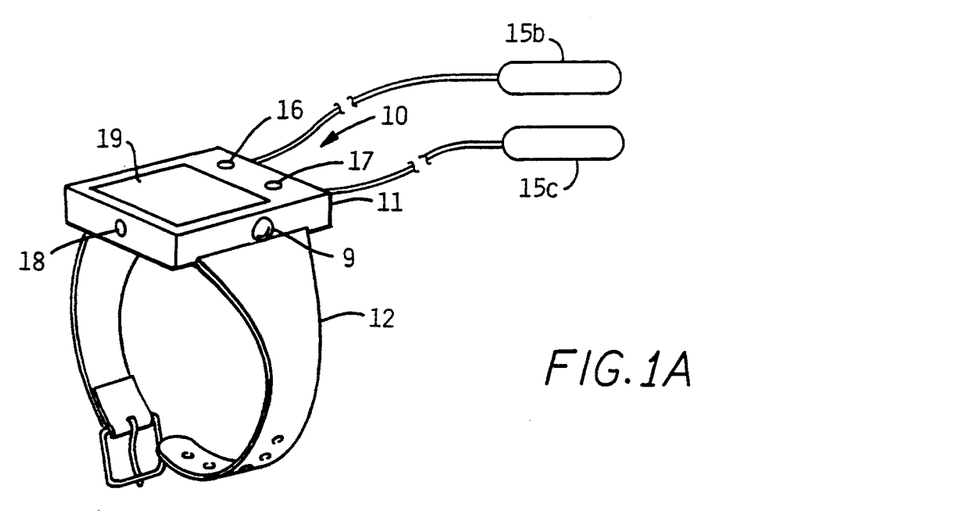
FIG. 1A is a perspective view of a portable ECG monitor/recorder exemplified by the present invention.

Turning now to the drawings, and referring first to FIG. 1A, there is shown a portable electrocardiographic (ECG) data monitor/recorder 10 which is adapted to be worn on the wrist of a user. This unit includes a casing 11 which houses the electronic circuitry and a wristband 12 for securing the casing to the user's wrist. The casing 11 includes an electrode, control buttons, an output port for coupling the unit to a modem device, and an LCD display for visually providing information to the user.

Figure 1B:
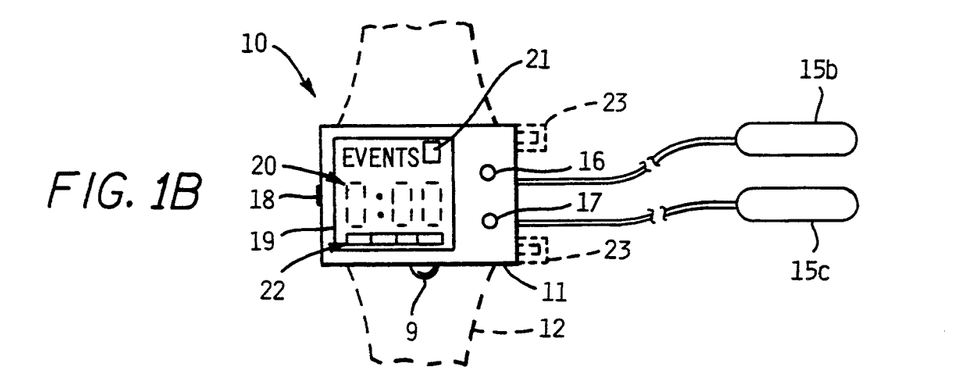
FIG. 1B is a top view of the ECG monitor/recorder of FIG. 1A.
Figure 1C:
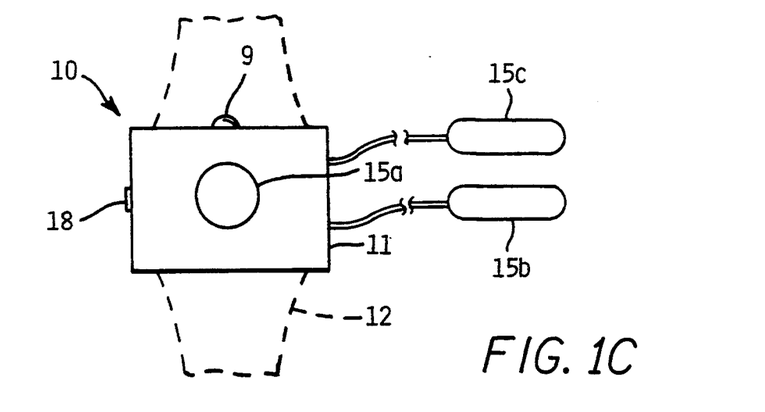
FIG. 1C is a bottom view of the ECG monitor/recorder of FIG. 1A.
Figure 1D:
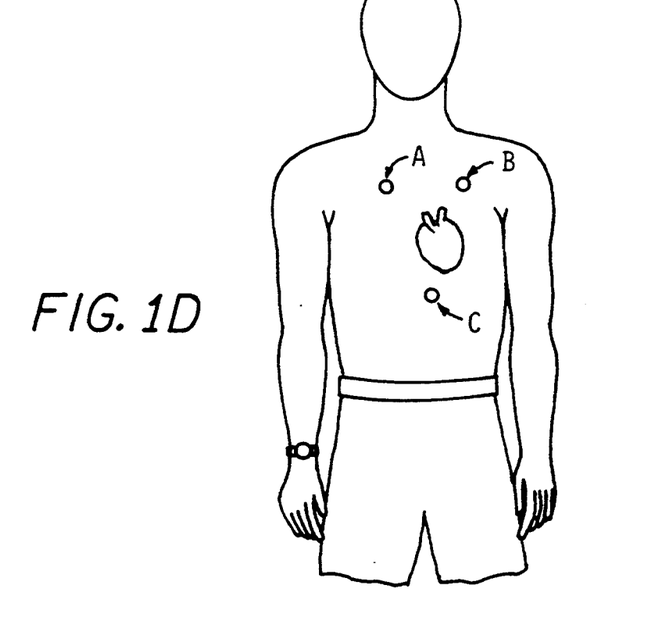
FIG. 1D shows the locations of the electrodes positioned on the body of the user of the ECG monitor/recorder of FIG. 1A.

As shown in FIGS. 1A–1C, a first conductive electrode 15a is provided on the bottom surface of the casing 11, where it is held in constant contact with the user's wrist when the unit is worn. Another pair of conductive electrodes 15b, 15c are provided external to the casing 11, where they can be easily attached to the user's chest at positions B and C, respectively, as shown in FIG. 1D. The conductive electrodes 15b and 15c are operatively connected to the electronic circuitry contained in the casing 11. As such, a circuit is completed which is capable of recording ECG data, as will be described in further detail hereinafter. Positions A, B and C in FIG. 1D form a standard lead configuration (commonly referred to as an Eindhoven triangle) used to measure ECG data. However, by positioning the electrode 15a on the user's wrist, an actual paste-on electrode at position A is not required. Determining the differentials between positions B and A or between positions C and A is achieved by measuring the differentials between electrodes 15b and 15a and between electrodes 15c and 15a, respectively. By using an electrode positioned on the user's wrist, the number of paste-on electrodes required to complete the Eindhoven triangle is minimized.

The three electrodes are made of a suitable conducting material, preferably silver or silver chloride. To enhance the electrical contact between the electrodes and the user's skin, the user typically prepares the skin contact area by applying an appropriate contact cream or gel (or even water or saliva) before securing the electrodes.

The unit further includes a pair of push-buttons 16, 17 on its top surface, one of which is used to clear the unit's memory (the mode button) and the other being used to transmit data stored in the memory to a separate modem device via serial output port 18 (the transmit button). In addition, an event button 9 is provided which the user pushes at the on-set of an episodic event.

An LCD display 19 is provided on the top surface of the casing. This display visually provides information to the user, preferably including an indicator 20 of the time of day, an indicator 21 of the number of cardiac events (e.g., arrhythmias) recorded, and a bar graph 22 which indicates the portion of the total memory that is filled with data.

While the inventive ECG monitor/recorder will preferably be used in an embodiment having a wristband for securing the casing to the user's wrist (as shown in FIG. 1A), it will be readily appreciated that the unit is easily adapted so that it can be worn by the user as a pendant. Specifically, rather than having a wristband 12, the casing 11 is provided with a pair of integral eyelets 23 (shown in phantom in FIG. 1B) for attachment to a cord or chain so that the unit can be hung around the user's neck. As such, the first electrode 15a is disposed to facilitate electrical contact with an ECG lead position on the user's chest, for example, at position C as shown in FIG. 1D. Then, to complete the Eindhoven triangle, the other two electrodes 15b, 15c can be attached to the user's chest at positions A and B, respectively.

By using the standard Eindhoven triangle configuration, six different channels (from the six standard ECG lead configurations) of ECG data may be obtained: (1) the standard Lead I configuration measuring the differential between positions A and B, (2) the standard Lead II configuration measuring the differential between positions B and C, (3) the standard Lead III configuration measuring the differential between positions C and A, (4) the standard AVL configuration measuring the differential between the average signals at positions C and A with the signal at position B, (5) the standard AVR configuration measuring the differential between the average signals at positions B and C with the signal at position A, and (6) the standard AVF configuration measuring the differential between the average signals at positions B and A with the signal at position C.

Figure 2A:
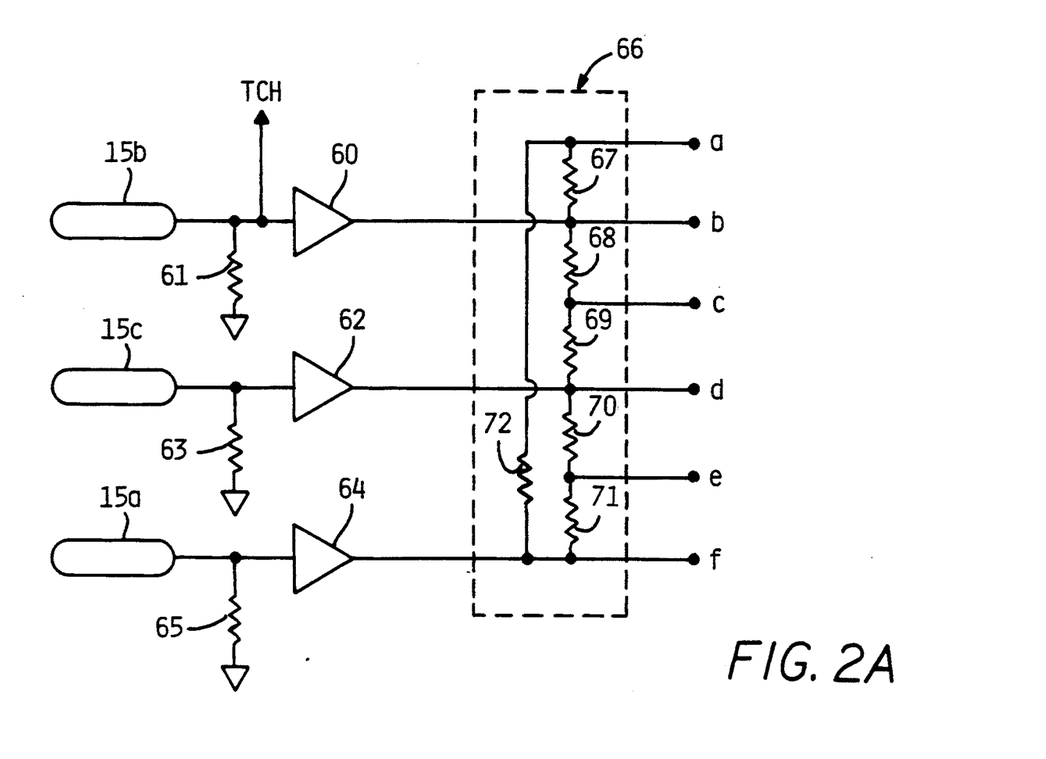
FIGS. 2A and 2B are circuit diagrams illustrating the electronic components of a portable ECG monitor/recorder exemplified by the present invention.
Figures 2B, 2D:
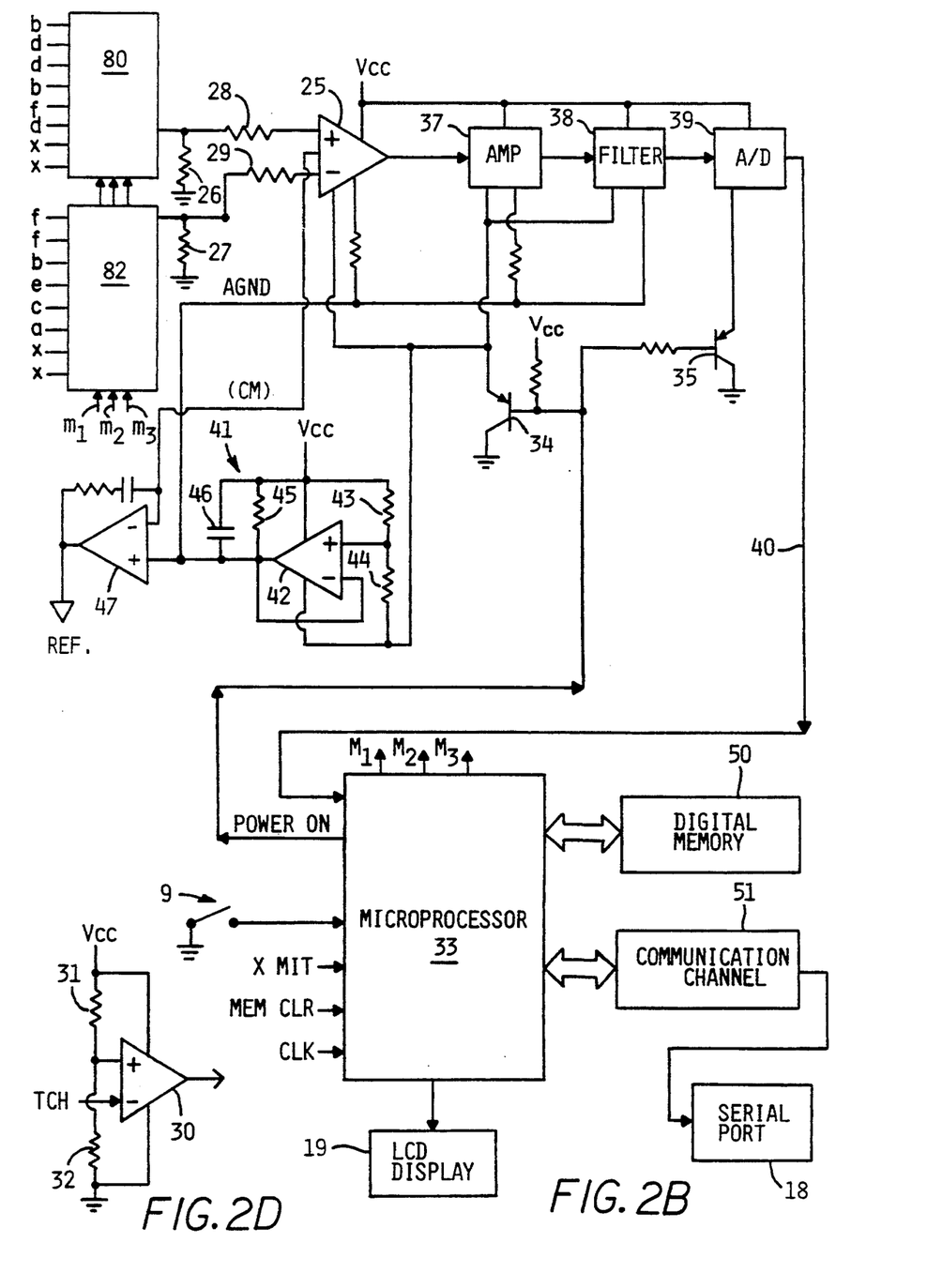
FIG. 2D is a circuit diagram illustrating a touch sensor used in an alternate embodiment of the ECG monitor/recorder in place of the switch 9 depicted in FIG. 2B.

FIGS. 2A and 2B illustrate the electronic components and circuitry contained in the casing 11 of the portable ECG data monitor/recorder. As shown in FIG. 2A, the conductive electrodes 15a, 15b and 15c are buffered through unity gain buffers 60, 62 and 64. Resistors 61, 63 and 65 (preferably 22M $\Omega$ each) are interposed between the "hot" electrodes 15a, 15b and 15c and ground and provide the circuit with a high input impedance. As described above, the following six signals are used to obtain the six standard ECG lead configurations: (1) the signal at electrode 15a, (2) the signal at electrode 15b, (3) the signal at electrode 15c, (4) the average of the signals at electrodes 15a and 15b, (5) the average of the signals at electrodes 15b and 15c, and (6) the average of the signals at electrodes 15a and 15c. To obtain these six signals, the outputs of the unity gain buffers are applied to a resistance summing network 66.

The resistance summing network 66 is comprised of six resistors (resistors 67 through 72) of equal resistance (preferably 0.1M $\Omega$). As shown in FIG. 2A, the signal at electrode 15a passes through the resistance summing network 66 and is provided as output "f." Similarly, the signals at electrodes 15b and 15c pass through the resistance summing network 66 and are provided as outputs "b" and "d," respectively. The resistance summing network 66 averages the signals at electrodes 15a and 15b, and this average signal for electrodes 15a and 15b is provided as output "a." Similarly, the resistance summing network 66 averages the signals at electrodes 15b and 15c, and averages the signals at 15a and 15c. These average signals for electrodes 15b and 15c and for electrodes 15a and 15c are provided as outputs "c" and "e," respectively In accordance with an important aspect of the present invention (shown in FIG. 2B), the outputs ("a" through "f") of the resistance summing network 66 are applied to certain predetermined inputs of a pair of conventional analog 8-to-1 multiplexers 80, 82. Three binary select signals M1, M2 and M3 are simultaneously generated by the microprocessor 33 to select the outputs of the multiplexers, the values of the select signals depending upon the desired lead configuration.

For example, to obtain ECG data measurements across the standard Lead I configuration, the signals at electrodes 15a and 15b are needed. As previously described, the signal at electrode 15a is provided as output "f" of the resistance summing network 66. Output "f" is supplied to the fifth (in this embodiment, binary 100) input of the first multiplexer 80 and to both the first (000) and second (001) inputs of the second multiplexer 82. Similarly, the signal at electrode 15b is provided as output "b" of the resistance summing network 66, which output is supplied to both the first (000) and fourth (011) inputs of the first multiplexer 80 and the third (010) input of the second multiplexer 82. Accordingly, to select the signals at electrodes 15a and 15b as the outputs of the two multiplexers, the microprocessor 33 is programmed to set the value of each of the select signals M1, M2 and M3 at binary zero. The resulting 3-bit select signal—000—causes each of the two multiplexers to output the signal supplied at its first (000) input (i.e., output "f" for multiplexer 80 and output "b" for multiplexer 82).

Figure 2C:
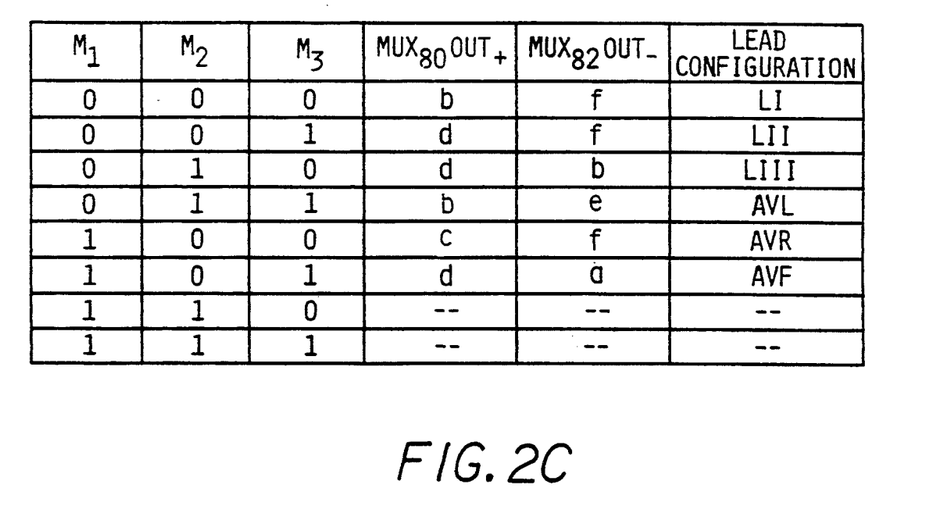
FIG. 2C is a chart showing the values of select lines M1, M2 and M3 for each of six lead configurations which are possible by a portable ECG monitor/recorder exemplified by the present invention.

A similar selection process is used for the other five standard lead configurations. By changing the values of the three select signals, the ECG recorder 10 can record ECG data from any one of the multiple data input channels. A table showing values of the select signals M1, M2 and M3 required to obtain each standard lead configuration is shown in FIG. 2C.

Referring again to FIG. 2B, a pair of resistors 28, 29 (preferably 1M Ω each) are positioned between the multiplexers 80, 82 and the inputs of an instrument amplifier 25 and provide a simple patient protection/electrostatic discharge (ESD) network which protects the electronic circuitry from static discharge from the user and limits the maximum battery current applied to the user to approximately 2 microamps.

A "power on" signal (having a logic zero value) provided by the microprocessor 33 is applied to the base terminals of a pair of pnp type transistors 34, 35. These transistors are normally biased to an OFF condition due to the connection of the power supply $V_{cc}$ to their base terminals, but application of the logic zero "power on" signal to their bases turns them ON. This enables various electronic components in the signal processing circuitry.

As described previously, a selected analog ECG data signal is applied to the inputs of the instrument amplifier 25. As a result of the arrangement shown, a high common mode rejection ratio is achieved. The resistor 36 serves as a gain control. This amplifier arrangement also permits overall simplification of the circuitry, since only one amplifier is needed to get satisfactory performance. As will be appreciated, this significantly reduces the power consumption and spatial requirements of the circuit.

The output of instrument amplifier 25 is applied to a second amplifier 37, which is configured in a typical feedback arrangement to provide a desired gain (for example, 4). The output of amplifier 37 is delivered to a standard monitor quality bandpass filter 38, consisting of a 40 Hz lowpass filter (which eliminates some muscle artifact and 60 Hz interference), followed by a 0.5 Hz multiple feedback highpass filter (which minimizes baseline wander). Finally, the signal is digitized by an 8-bit analog-to-digital converter (A/D) 39 and is supplied via data line 40 to the microprocessor 33.

A driver circuit 41, consisting of an amplifier 42, three resistors 43–45, and a capacitor 46, provide the amplifiers 25, 37 and filter circuit 38 with an analog ground (AGND) signal. A common mode (CM) signal, representing the summation of the two common mode inputs to instrument amplifier 25 is applied to an amplifier 47 along with the AGND signal. Accordingly, the value of the resulting reference signal (REF) is variable and dependent upon the selected inputs to the instrument amplifier 25.

During normal operation of the ECG data monitor/recorder 10, the microprocessor receives ECG data from the 8-bit A/D converter 39 and stores it in sequential memory address locations in a digital memory device 50. This memory device preferably consists of a $32K \times 8$ static random access memory (SRAM), but it will be readily appreciated that the memory device could satisfactorily consist of a flash-EPROM or any read/write memory circuit configured as a first in/first out (FIFO) ring memory. The microprocessor 33 (which, for example, may consist of an NEC 75308 processor) samples digitized data from the A/D converter 30 every 10 milliseconds and, therefore, assuming the memory device 50 is a $32K \times 8$ SRAM, over four minutes of data can be stored.

As described above, the microprocessor 33 selectively records any one of the six channels of input by setting the select signals M1, M2 and M3 at values which correspond to the desired lead configuration. In a preferred embodiment of the present invention, a record data counter causes switching of the input channel at ten second intervals. Accordingly, in a one minute cycle, all six input channels will be recorded. To distinguish between data recorded from the different input channels, a unique marker is inserted into the data at the beginning of recording from each channel.

It will be appreciated that although six different channels of data are available, it is not necessary to record data from each channel for the same duration of time. Nor is it even necessary to record data from all six channels. Depending upon the individual user's condition, it may be desirable to record ECG data from only certain channels and for different durations of time, both before and after the on-set of an episodic event. For example, before the on-set of an episodic event, it may be desirable to monitor and record a user's ECG data from only the standard Lead I configuration (channel 1) and the standard AVF configuration (channel 6) in alternating ten second increments, whereas after the on-set of an episodic event it may further be desirable to monitor and record short segments of the user's ECG data from the standard Lead II (channel 2) and the standard Lead III (channel 3) configurations—such that each recording cycle after the on-set of an event includes ten seconds from channel 1, ten seconds from channel 6, five seconds from channel 2 and five seconds from channel 3. In order to achieve such recording versatility, an important aspect of the present invention provides for the selection of such combinations or "profiles." By pressing and continuously holding down the mode button for a period of 3 seconds, the user enters into a program mode where the user (or the user's doctor) may select any one of a number of profile options.

Again, in normal operation of the ECG data monitor/recorder 10, the recording of ECG data is continuous. However, since the memory capacity of the recorder is limited, a circular buffer is used to record and preserve the most current data while overwriting older data. At the on-set of an episodic event, the user presses the event button 9 (shown as a mechanical switch in FIG. 2B) which signals the microprocessor 33 both to preserve a predetermined quantity of data which was recorded before the event button 9 was pressed and to stop recording additional data after a predetermined amount of time or memory has elapsed. During the program mode, the user may select the specific quantity of data stored before and after the event button is pressed. In certain preferred embodiments of the present invention, the user may choose to preserve either 120, 150 or 180 seconds of previously recorded data. Then, subsequent ECG data is recorded and saved until the buffer becomes full. If the event button 9 is pressed before the minimum amount of data is stored, all previously recorded data is preserved and the remaining amount of the buffer is filled with subsequent data. In a preferred embodiment of the present invention, multiple event buffers are available to store ECG data relating to multiple different episodic events.

The microprocessor operates in a playback (or transmit) mode when it receives a logic zero "transmit" signal (XMIT), which is generated when the user depresses the control button 16. In this playback mode, the microprocessor sequentially fetches the digitized ECG data from the digital memory device 50 and sends it to the serial port 18 in burst mode via a communication channel 51.

If the user depresses the second control button 17, a logic zero "memory clear" signal (MEM CLR) is provided to the microprocessor. If this signal is received simultaneously with depression of the "transmit" control button 16 by the user, the microprocessor instantaneously clears the digital memory 50 by resetting an internal write pointer to the starting base address of the memory. As will be appreciated, making the "memory clear" (mode) button 17 a slave to the "transmit" button 16 protects against accidental or inadvertent erasure of data.

Finally, the microprocessor also generates the information and provides the drive signals for the LCD display 19. These functions are executed under instructions from standard built-in firmware (not shown) in the microprocessor's internal memory.

Figure 3A:
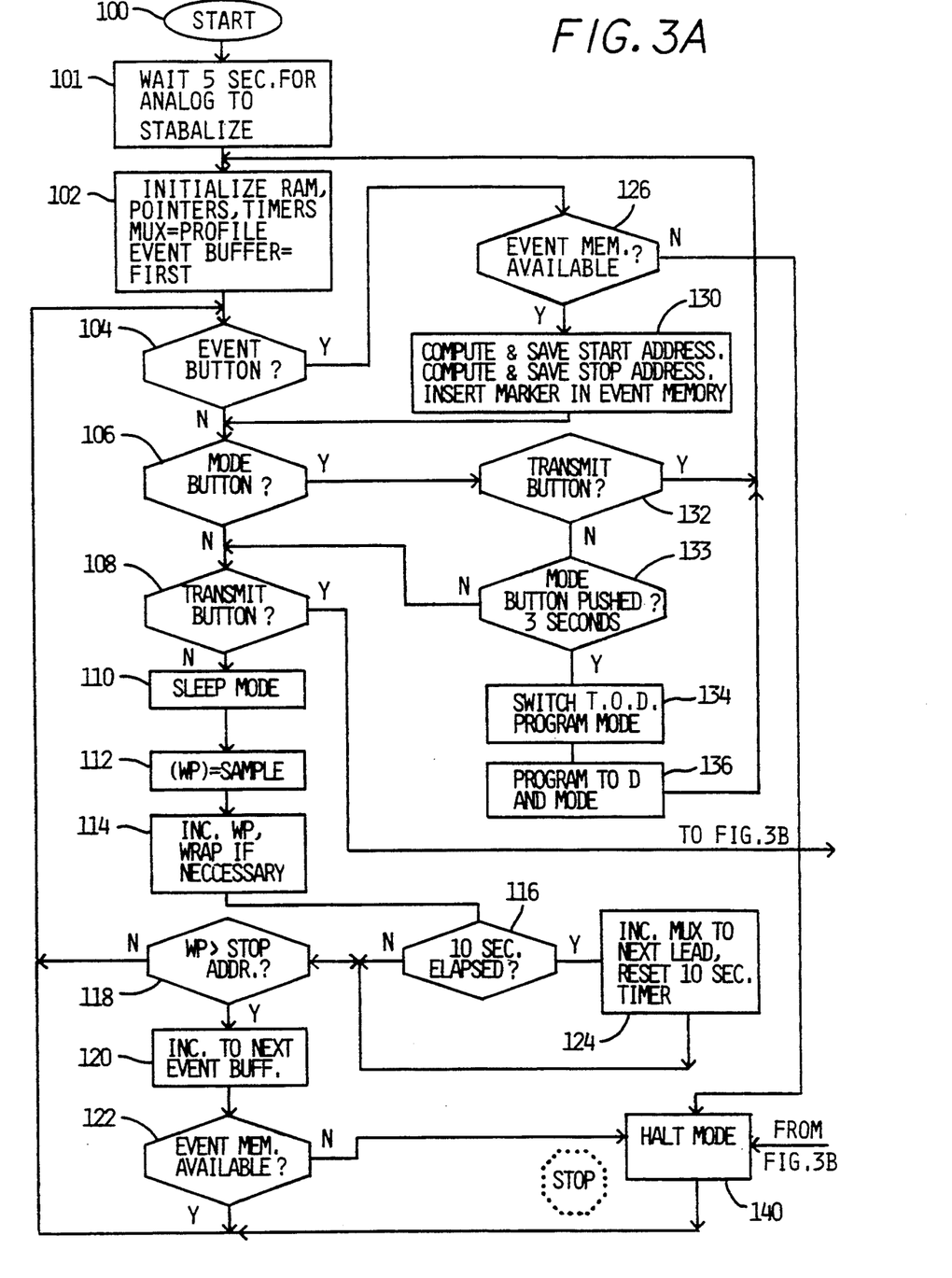
FIGS. 3A and 3B are flow chart representations of a preferred sequence of operations followed by the microprocessor of the inventive ECG monitor/recorder of FIGS. 2A and 2B.
Figure 3B:
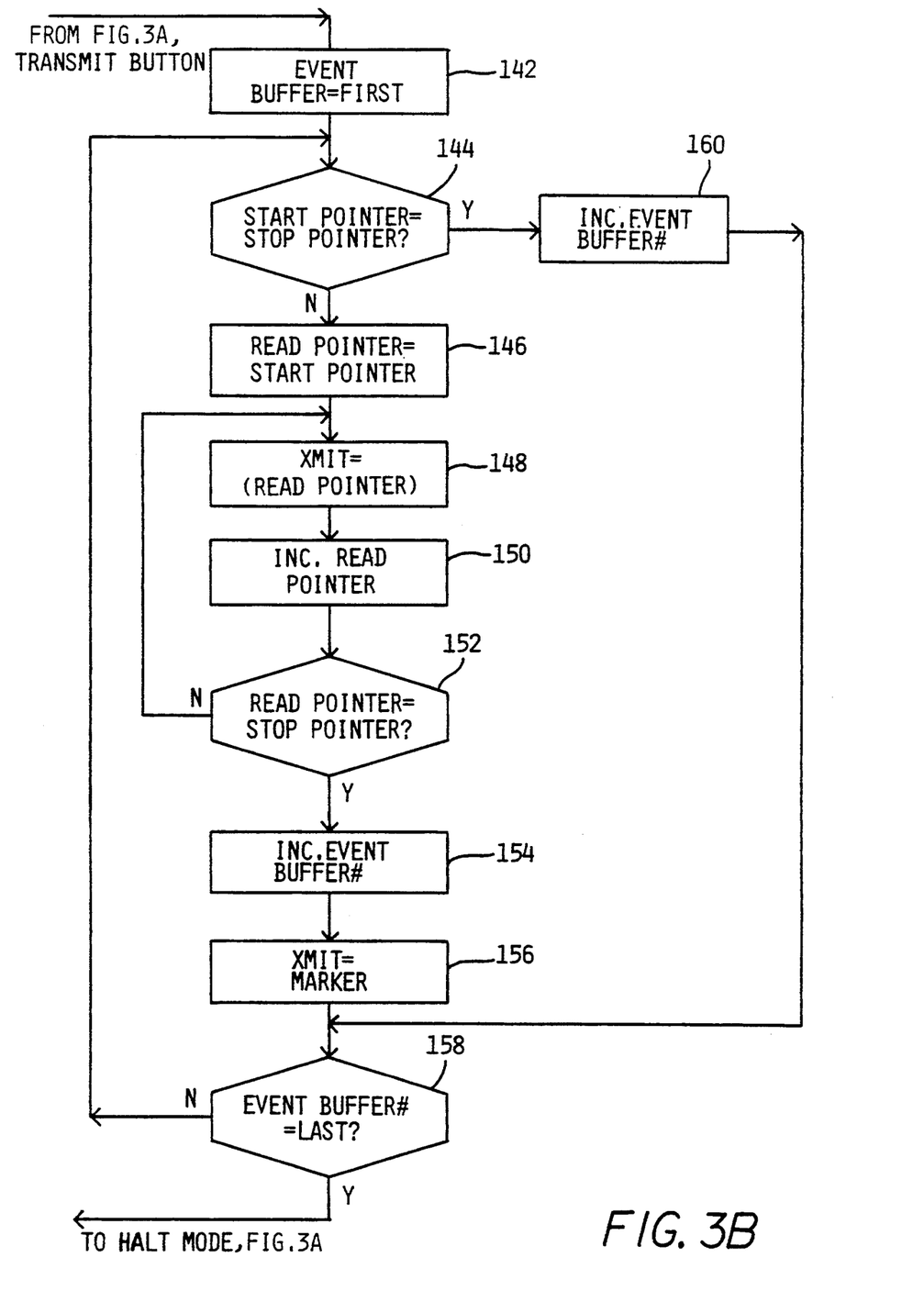

The sequence of operations followed by the microprocessor 33 in the inventive ECG data monitor/recorder is illustrated in further detail by the flow charts of FIGS. 3A and 3B. Specifically, the flow charts illustrate the record, transmit and memory clear modes of operation. When batteries are put in the device (step 100), the microprocessor waits 5 seconds for the analog signals to stabilize (step 101) and initializes the circuit components (step 102). This initialization includes setting both the read pointer and write pointer of the memory device 50 to a starting base (0) address, initializing the communication channel 51 to a master transmitter mode and initializing the port pins to minimize power consumption. The initialization step 102 also sets an event buffer pointer to the first event buffer and the multiplexer profile selector, MUX, to an initial profile. After this is done, the microprocessor goes into normal record mode operation in which it continuously records the ECG data of the user until an interrupt signal is received.

In sampling for interrupt signals, at steps 104, 106 and 108 the microprocessor determines the logic condition of the output signals of the event button, the memory clear button and the transmit button, respectively. If the signals are low, indicating that the user has not pushed any of the buttons, the microprocessor goes into a low power sleep mode (step 110). The user's analog ECG signal is then digitized, as discussed previously, and provided to the microprocessor on data line 40. The lower power sleep mode is terminated by a 10 millisecond sampling cycle timer tick. Then, the microprocessor reads the digitized output of the A/D converter 39 after 10 milliseconds have elapsed and sequentially writes the digitized ECG data to both the memory device 50 and the communication channel 51 in real time mode (step 112). The write-pointer is then incremented at step 114. If the write-pointer is pointing at the last memory address of the buffer, instead of incrementing the write-pointer, it is reset to zero, thereby wrapping the write-pointer back to the beginning of the buffer.

At step 116, the microprocessor increments the record data counter and determines whether 10 seconds have elapsed while recording on the same input channel. If so, at step 124, the MUX pointer is incremented to the next input channel and the record data counter is reset to zero. In addition, a unique marker is inserted into the buffer to identify the new input channel data. At step 118, the microprocessor determines whether the write-pointer is greater than the stop address. If it is not, the sequence of operations returns to step 104 to continue recording ECG data.

If, at step 104, it is determined that the user has pressed the event button, the microprocessor checks to make sure that event memory is available (step 126). If so, at step 130, the microprocessor computes and saves the recording start and stop addresses and inserts a marker into the memory buffer to identify that the event button was pressed. The start address is calculated by subtracting a preset offset from the current write-pointer memory address. Similarly, the stop address is calculated by adding an off-set to the current write-pointer memory address. The value of the offsets are dependent upon the amount of data which is to preserved and recorded before and after the event button is pressed. The calculation of the start and stop addresses also depends upon whether wrapping around the memory is necessary.

After the event button is pressed, subsequent depressions of the event button are ignored and data continues to be recorded until the write-pointer becomes greater than the stop address. When this occurs, the current event buffer is full and an event buffer pointer is incremented to the next event buffer at step 120. If an additional event buffer is unavailable (step 122), the microprocessor goes into halt mode (step 140). At this point, all memory is full and data needs to be transmitted (or cleared) before recording additional data.

The halt mode at step 140 is terminated when the user presses the memory clear or transmit buttons. At step 106, the microprocessor checks the logic condition of the "memory clear" (mode) button. If the "memory clear" button has been pressed, the microprocessor checks to see if the transmit button has also been pressed (step 132). If so, the microprocessor clears the memory in the buffers and re-initializes the circuit components (step 102). If not, the microprocessor checks a mode button counter at step 133 to see if the mode button has been pressed for a duration of 3 seconds. If so, the microprocessor stops recording data and switches into a program mode (step 136). During the program mode, the user may set the time of day (T.O.D.), select a desired profile, or select the specific quantity of data to be stored before and after the event button is pressed. Then, the microprocessor clears the memory in the buffers and re-initializes the circuit components in step 102 to begin recording ECG data.

At step 108, the microprocessor checks the logic condition of the "transmit" signal. When the "transmit" signal (XMIT) is low, indicating that the user has depressed control button 16 and desires to transmit the stored ECG data to an external receiver, the microprocessor sets the event buffer pointer to the first event buffer (step 142). Next, at step 144, it is determined whether the address of the start pointer equals the stop pointer. If so, valid data does not exist in the current buffer and the event buffer pointer is incremented (step 160). If not, the read pointer is set to the value of the start pointer (step 144) and the contents of the memory at the read pointer address are read and written to the communication channel 51 in burst mode (step 148). By transmitting in burst mode, five minutes of data can be sent out of the serial port in less than ten seconds. It will be appreciated, therefore, that power consumption during transmission of data is kept to a minimum, which effectively doubles the battery life. This is significant inasmuch as the batteries are difficult to change and typically cannot be changed by the user.

Once data at the read pointer address has been written to the communication channel, the read pointer is incremented (step 150) and the read/write cycle is continued until all of the data has been transmitted, i.e., until the read pointer equals the stop pointer (step 152). As noted before, this entire data transmission procedure required less than ten seconds when the memory is full.

After all the memory has been transmitted from the current event buffer, the event buffer pointer is incremented at step 154 and a marker is transmitted at step 156 to signal the completion of the transmission for the current buffer. At step 158, the microprocessor checks to see if the data from the last event buffer has been transmitted. If not, the above transmission steps are repeated (beginning at step 144) until the data in each of the event buffers is transmitted. When all the data for each event buffer is transmitted, the microprocessor goes into halt mode at step 140.

In an alternate embodiment of the present invention, paste-on electrode 15b is not used. Electrode 15a and paste-on electrode 15c remain positioned as explained above and continue to form the standard Lead II configuration. However, instead of using the second paste-on electrode 15b, the event button 9 (on the side surface of the casing 11) is configured as the third conductive electrode ("event button electrode 9"). The standard Eindhoven triangle is completed when the user contacts the event button electrode 9 with the user's left thumb or forefinger (assuming the unit is being worn on the right wrist). In this embodiment of the present invention, before the on-set of an episodic event, ECG data is continuously recorded from the Lead II configuration, which is the only data channel available at that point. By grasping and holding the event button electrode, the user completes the standard Eindhoven lead configuration. Data is then available from the six input channels as described above. To reduce undesirable electrode-skin artifact "noise" signals arising from contact variations, the event button electrode 9 is substantially circular or oval (as opposed to square or rectangular), is small enough in size to be covered completely by the user's finger and/or thumb, and has a curved (as opposed to flat) surface geometry.

In this alternate embodiment, the mechanical switch 9 shown in FIG. 2B is replaced by the circuitry in FIG. 2D. Upon contact of the event button electrode (illustrated as electrode 15b in FIG. 2A) by the user, a touch signal (TCH) is generated and applied to the inverting input of a comparator 30 of FIG. 2D, which serves as a touch sensor. A divider network consisting of two resistors 31, 32 provides current from the power supply ($V_{cc}$)—preferably consisting of two 3 V lithium coin cell batteries wired in parallel—to the non-inverting input of the comparator 30. Since the inverting input is normally low, the output of the comparator is normally high (i.e., logic one). When the touch signal (TCH) is generated, the inverting input goes high and causes the output of the comparator 30 to go to logic zero. The signal from the comparator 30 is applied to an input of a microprocessor 33, which signals the microprocessor that the user has contacted event button electrode 9, i.e., that an event has occurred. The microprocessor 33 then outputs control signals so as to cause 1) a predetermined quantity of data which was recorded before the user pressed the event button electrode 9 to be preserved, 2) selective recording of data from one or more of the six channels of input which are available, and 3) recording of additional data to stop after a predetermined amount of time or memory has elapsed, as described more fully above.

Figure 4:
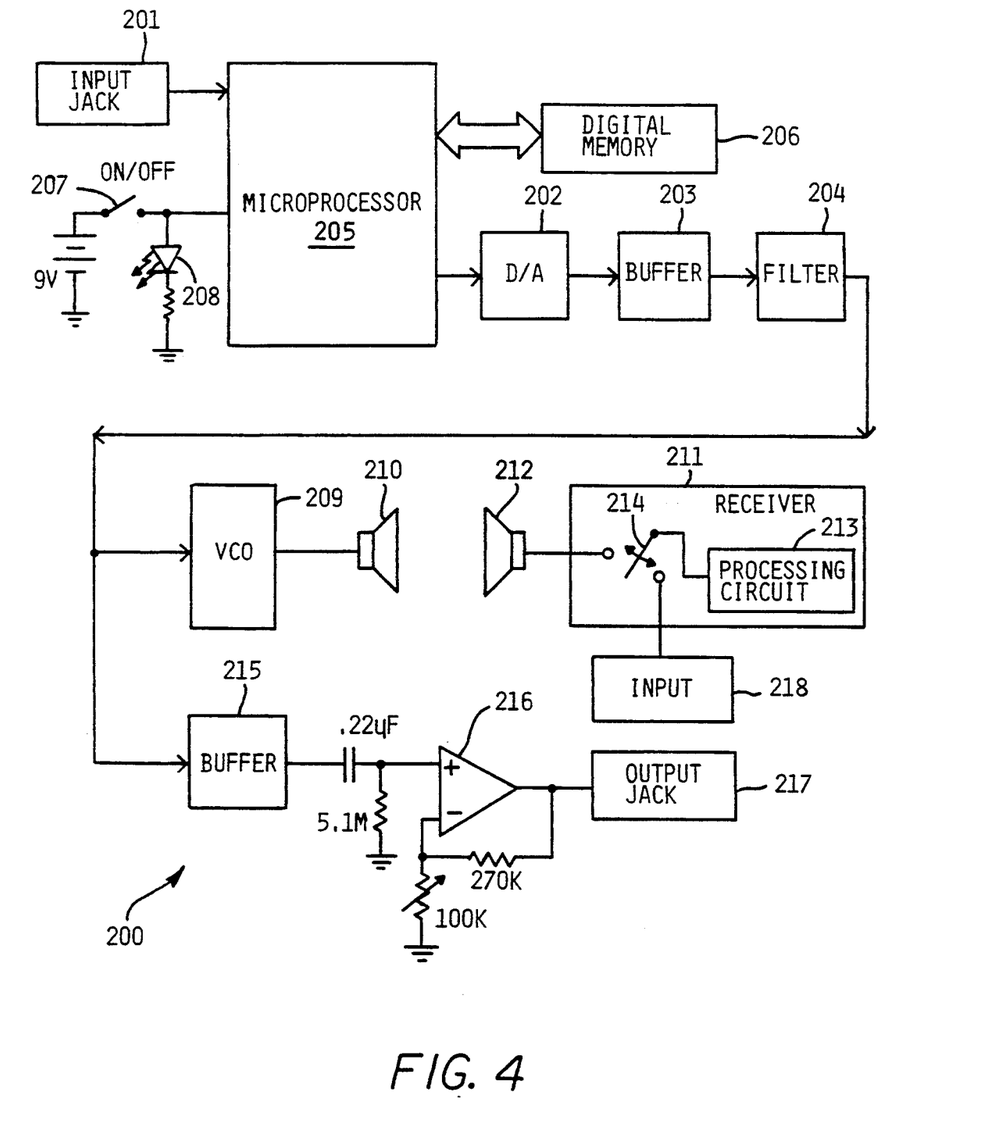
FIG. 4 is a circuit diagram of a data-converting modem for use in conjunction with the ECG monitor/recorder of FIG. 2.

A modem device is provided which is adapted for electrical connection to the ECG data monitor/recorder 10 and includes components for receiving the digitized ECG data stored in the recorder's memory 50, processing that data into a format which can be transmitted for analysis to an external receiver, and transmitting the processed data to the external receiver. The circuit diagram of FIG. 4 illustrates the components of this modem, which is designated generally by reference numeral 200. In a preferred embodiment, the modem device 200 is separate from the ECG data monitor/recorder 10, and has an input jack 201 which is adapted to mate with the output serial port 18 of the recorder 10 so that data transfer can be effected. The digitized ECG data from the recorder memory 50 is converted into analog signals having discrete voltage levels by a standard digital-to-analog converter (D/A) 202. Every 10 milliseconds, this D/A converter converts a data byte to a discrete voltage level. This voltage level is applied to a buffer 203 and an anti-aliasing 40 Hz lowpass filter 204 that smooths the voltage waveform back to its original analog shape.

The modem 200 includes a microprocessor 205 (for example, an Intel 80C51 processor) and a digital memory 206 (which is preferably an SRAM or an EPROM). A power source consisting of a common nine volt alkaline battery is coupled to the microprocessor through a switch 207, by means of which the user can turn the microprocessor (and, thus, the modem itself) on and off. An LED 208 provides a visual indicator to the user that the microprocessor 205 is being powered.

The microprocessor receives serial data from the recorder 10 via the serial input jack 201. This serial data is converted to 8-bit parallel (byte-wide) information by internal serial channel hardware., which data byte is then an exact copy of the sampled ECG data acquired by the recorder 10. The microprocessor 205 then stores the ECG data byte in the SRAM memory 206, and loops back to receive the next byte from the internal serial channel hardware.

Every 10 milliseconds, an internal timer generates an interrupt signal that directs the microprocessor 205 to fetch the next sequential byte of ECG data from the SRAM memory 206 and send it to the D/A converter 202. Because the D/A converter 202 can only reconstruct the sampled ECG waveforms at a rate of 1 byte every 10 milliseconds, burst mode transmission of data from the recorder 10 to the modem 200 would be impossible without the microprocessor 205 and the SRAM memory 206. The SRAM memory is used as an ECG data buffer, so that the recorder-to-modem data transmission can occur at a higher speed than the real-time playback of the modem, without inter-device synchronization problems.

The analog output of the filter 204 is fed to a voltage controlled oscillator (VCO) 209 that has a center frequency of 1900 Hz. The VCO 209 is calibrated such that its frequency deviates 100 Hz from its center frequency for every one millivolt change in the analog ECG waveform.

The output of the VCO 209 is coupled to a speaker 210, by means of which frequency modulated tones are audibly transmitted. An external receiver 211, such as an ECG monitor in a physician's office, may receive the frequency modulated tones from the speaker 210 via an appropriate audio receiver 212 (e.g., a telephone receiver). The received audio signals are then provided to processing circuitry 213 in the receiver 211 via a switching mechanism 214.

In the preferred embodiment, the modem 200 further includes a unity gain buffer 215 and an amplifier circuit (generally designated by reference numeral 216) which produces an output signal having an amplitude of 1 volt per millivolt amplitude in the analog ECG waveform received from the filter 204. This output signal is provided to an output jack 217 which may be coupled to a corresponding input jack 218 on the receiver 211 for effecting data transfer.

In an alternative embodiment, the ECG data monitor/recorder and the modem device comprise a single unit (or are capable of being joined into a single unit). This, of course, increases the size of the unit, but simplifies the data transmission process for the user (which may be important following a cardiac event).

Figure 5:
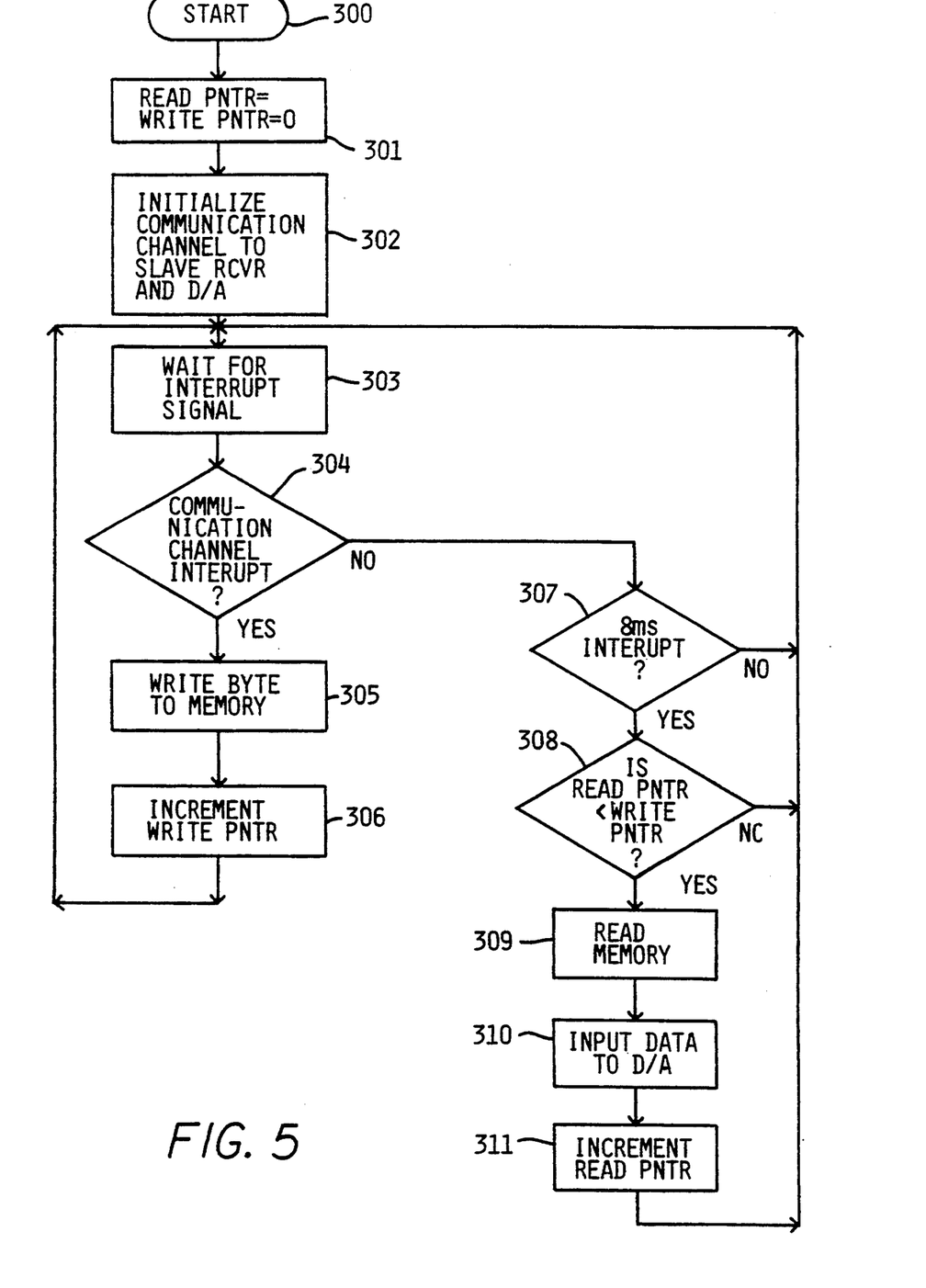
FIG. 5 is a flow chart representation of a preferred sequence of operations followed by the modem of FIG. 4.

The sequence of operations followed by the microprocessor 205 in the modem 200 is illustrated in further detail by the flow chart of FIG. 5. When the switch 207 is closed and the microprocessor is turned on (step 300), the microprocessor sets both the read pointer and write pointer of the memory device 206 to a starting base (0) address (step 301), initializes the communication channel to a slave receiver mode and initializes the D/A converter 202 (step 302). The modem then awaits for an interrupt signal (step 303). If an interrupt signal is received from the communication channel (step 304), an ECG data byte is written to the memory 206 (step 305) and the internal write pointer in the memory is incremented (step 306). This loop continues until the entire data sequence from the recorder is received and written to the memory 206 in the modem.

With respect to transmission of the data stored in the memory 206, when a 10 millisecond interrupt signal is received at step 307 and it is determined that the address of the internal write pointer is greater than the address of the internal read pointer (step 308), the sequential byte of ECG data stored at the read pointer address of the memory 206 is read (step 309). This byte of data is then sent to the D/A converter 202 for processing (step 310) and the internal read pointer is incremented (step 311). This loop is continued, with 10 millisecond sampling, until all of the data stored in memory 206 has been processed (i.e., until the read pointer address is the same as the write pointer address).

As can be seen from the foregoing detailed description, the present invention provides an improved apparatus for continuously recording medical-grade ECG data—selectively from any of six standard lead configurations—and yet which minimizes the number of paste-on electrodes that are required, thereby providing an apparatus that is convenient and comfortable for a user to wear. The inventive recorder has a high common mode rejection ratio due to the use of a three electrode configuration and a unique amplifier arrangement, and the design of the processing circuits insures long battery life. A modem device is provided for transmitting stored data from the recorder to a receiving station. This modem, which is preferably a separate attachable device, enables transfer of data from the recorder in power-saving burst mode.

What is claimed is:

1. A portable, encased apparatus having electronic circuitry for continuously monitoring a user's electrocardiographic (ECG) data signals, said apparatus comprising:

a first conductive electrode coupled to the electronic circuitry and disposed on a surface of the apparatus casing so as to facilitate electrical contact with a first of three ECG lead positions which constitute an Eindoven's triangle on the user's body, wherein a wristband is provided for securing the casing to a wrist of the user and the first conductive electrode is disposed on the back surface of the casing such that it lies in continuous electrical contact with the user's wrist;

a second conductive electrode coupled to the electronic circuitry and adapted to facilitate continuous electrical contact with the user's body in a second Eindoven's triangle ECG lead position, the second electrode being separate from the apparatus casing; and a third conductive electrode coupled to the electronic circuitry and adapted to facilitate electrical contact with the user's body in a third Eindoven's triangle ECG lead position;

wherein the electronic circuitry includes a microprocessor which controls selective monitoring of the user's ECG data signals from one or more of six standard Eindoven's triangle ECG lead configurations when each of the three electrodes is in electrical contact with its associated ECG lead position on the user's body.

2. The apparatus of claim 1, wherein the second conductive electrode comprises a paste-on electrode which is coupled to the electronic circuitry by means of an elongated conductive wire.

3. The apparatus of claim 1, wherein the third conductive electrode comprises a paste-on electrode which is coupled to the electronic circuitry by means of an elongated conductive wire.

4. The apparatus of claim 1, wherein the third electrode is disposed on a surface of the apparatus casing other than the surface on which the first electrode is disposed and is positioned for ease of contact by the hand of the user's arm which is nearest to the third Eindoven's triangle ECG lead position.

5. The apparatus of claim 1, wherein at least one of said first and third conductive electrodes is adapted so as to be in continuous contact with its associated ECG lead position, and the microprocessor controls the apparatus such that prior to the occurrence of a cardiac event the user's ECG data signals are monitored continuously using the electrodes which are in continuous contact with ECG lead positions on the user's body.

6. The apparatus of claim 1, wherein the microprocessor is programmable so as to permit a monitoring cycle to be selected which includes monitoring of the user's ECG data signals from any or all of the six standard Eindoven's triangle ECG lead configurations in a pre-set sequence.

7. The apparatus of claim 6, wherein the microprocessor is further programmable so as to permit the monitoring cycle to be adjusted so that ECG data signals are monitored from each of the selected ECG lead configurations for a respective pre-set portion of the cycle.

8. The apparatus of claim 1, further comprising an electronic indicator means for the user to contact to generate a signal indicating that a cardiac event has occurred.

9. The apparatus of claim 8, wherein said electronic indicator means is a pushbutton switch which is disposed on a surface of the apparatus casing and electrically coupled to the microprocessor.

10. The apparatus of claim 8, wherein the microprocessor is programmable so as to permit a monitoring cycle to be selected in which ECG data signals are sequentially monitored from a first selected set of one or more of the six standard Eindoven's triangle ECG lead configurations until the user contacts said electronic indicator means, and after the user contacts said electronic indicator means, post-event ECG data signals are sequentially monitored from a second selected set of one or more of the six standard ECG lead configurations.

11. The apparatus of claim 10, wherein the electronic circuitry further comprises:

a power source;

circuit means coupled to the power source and the electrodes for receiving the user's analog ECG signals from one or more of six standard Eindoven's triangle lead configurations and for converting such signals into digitized format; and memory for receiving and storing the digitized ECG data;

wherein said microprocessor further controls storage of the digitized ECG data into the memory such that, digitized ECG data is continuously stored, with new data being cyclically recorded over older data when the memory becomes full, until the user contacts said electronic indicator means, and after the user contacts said electronic indicator means, a predetermined quantity of the most recently stored ECG data is retained in the memory and post-event ECG data is stored in the remainder of the memory.

12. The apparatus of claim 8, wherein said electronic indicator means is an electrode which is disposed on a surface of the apparatus casing and electrically coupled to the microprocessor.

13. The apparatus of claim 1, wherein the electronic circuitry further comprises:

a power source;

circuit means coupled to the power source and the electrodes for receiving the user's analog ECG signals from one or more of six standard Eindoven's triangle lead configurations and for converting such signals into digitized format; and memory for receiving and storing the digitized ECG data;

wherein said microprocessor further controls storage of the digitized ECG data into the memory.

14. The apparatus of claim 13, wherein said circuit means includes a resistance summing network which comprises:

three input lines, each of which is coupled to a different one of the three conductive electrodes;

six resistors of equal impedance; and six output lines, of which three are each connected directly to a different one of the three input lines, and of which the other three are each connected via a pair of resistors to a different pair of the three input lines.

15. The apparatus of claim 13, wherein at least one of said first and third conductive electrodes is adapted so as to be in continuous contact with its associated ECG lead position, and the microprocessor controls the apparatus such that prior to the occurrence of a cardiac event the user's analog ECG signals are monitored continuously using the electrodes which are in continuous contact with ECG lead positions on the user's body, the analog ECG signals are converted by the circuit means into digitized ECG data and the digitized ECG data is stored in the memory.

16. The apparatus of claim 13, further comprising an output which is coupled to the memory and adapted for transmission of the digitized ECG data to an external receiver, wherein the microprocessor, upon command of the user, controls the transmission of the digitized data from the memory to the external receiver via the output.

17. The apparatus of claim 16, further comprising a first command switch which, when closed by the user, provides a transmit signal to the microprocessor, whereupon the microprocessor initiates and controls transmission of the digitized data from the memory to the output.

18. The apparatus of claim 17, wherein the microprocessor transmits the digitized data stored in the memory to the output in burst mode, thereby minimizing power consumption.

19. The apparatus of claim 13, wherein the memory comprises a first in/first out ring memory.

20. The apparatus of claim 13, further comprising a modem device which is coupled to the memory and adapted to receive digitized ECG data from the memory and convert the data to a format suitable for transmission to an external receiving device.

21. The apparatus of claim 13, further comprising an output jack coupled to the memory and adapted for electrical connection to an input of an external receiving device.

22. A wrist-worn apparatus for continuously monitoring a user's electrocardiographic (ECG) data signals, said apparatus comprising:

a casing having front, back and side surfaces and a wristband which secures the casing to a wrist of the user;

a first conductive electrode disposed on the back surface of the casing such that it lies in continuous electrical contact with the user's wrist;

a second conductive electrode adapted to facilitate continuous electrical contact with the user's body in an Eindoven's triangle ECG lead position other than the one occupied by the first electrode, the second electrode being separate from the apparatus casing;

a third conductive electrode adapted to facilitate electrical contact with the user's body in an Eindoven's triangle ECG lead position other than the two occupied, respectively, by the first and second electrodes;

a power source;

circuit means electrically coupled to the power source and the electrodes for receiving the user's analog ECG signals and for converting such signals into digitized format;

memory for receiving and storing the digitized ECG data; and a microprocessor for controlling selective monitoring of the user's ECG data signals from one or more of six standard Eindoven's triangle ECG lead configurations when each of the three electrodes is in electrical contact with its respective ECG lead position on the user's body, and for controlling storage of the digitized ECG data in the memory.

23. The apparatus of claim 22, further comprising an electronic indicator means electrically coupled to the microprocessor for the user to contact to generate a signal indicating that a cardiac event has occurred, and wherein the microprocessor is programmable to permit a monitoring cycle to be selected in which prior to contact of the electronic indicator means by the user, ECG data signals are sequentially monitored from a first selected set of one or more of the six standard Eindoven's triangle ECG lead configurations, and after contact of the electronic indicator means by the user, post-event ECG data signals are sequentially monitored from a second selected set of one or more of the six standard ECG lead configurations.

24. A method for continuously monitoring and recording a user's electrocardiographic (ECG) data signals, comprising:

monitoring the user's analog ECG data signals by means of first, second and third conductive electrodes positioned, respectively, at first, second and third ECG lead positions which constitute an Eindoven's triangle on the user's body, of which at least one electrode is disposed on a surface of a wrist-worn casing such that it lies in continuous electrical contact with the user's wrist;

controlling the monitoring of the user's analog ECG data signals with a programmable microprocessor enclosed in the wrist-worn casing, whereby ECG data signals are sequentially monitored from a first selected set of one or more of the six standard Eindoven's triangle ECG lead configurations prior to receipt by the microprocessor of a signal indicating the occurrence of a cardiac event, and after receipt by the microprocessor of a signal indicating the occurrence of a cardiac event sequentially monitoring ECG data signals from a second selected set of one or more of the six standard Eindoven's triangle ECG lead configurations;

converting the monitored analog ECG data signals into a digitized data format utilizing electronic circuitry enclosed in the wrist-worn casing; and storing the digitized data in a memory enclosed in the wrist-worn casing.

25. A portable, encased apparatus having electronic circuitry for continuously monitoring a user's electrocardiographic (ECG) data signals, said apparatus comprising:

a first conductive electrode coupled to the electronic circuitry and disposed on a surface of the apparatus casing so as to facilitate electrical contact with a first of three ECG lead positions which constitute an Eindoven's triangle on the user's body, wherein the casing is adapted such that the apparatus may be worn by the user as a pendant, the first conductive electrode being disposed to facilitate electrical contact with an ECG lead position on the user's chest;

a second conductive electrode coupled to the electronic circuitry and adapted to facilitate continuous electrical contact with the user's body in a second Eindoven's triangle ECG lead position, the second electrode being separate from the apparatus casing; and a third conductive electrode coupled to the electronic circuitry and adapted to facilitate electrical contact with the user's body in a third Eindoven's triangle ECG lead position;

wherein the electronic circuitry includes a microprocessor which controls selective monitoring of the user's ECG data signals from one or more of six standard Eindoven's triangle ECG lead configurations when each of the three electrodes is in electrical contact with its associated ECG lead position on the user's body.

26. A portable, encased apparatus having electronic circuitry for continuously monitoring a user's electrocardiographic (ECG) data signals, said apparatus comprising:

a first conductive electrode coupled to the electronic circuitry and disposed on a surface of the apparatus casing so as to facilitate electrical contact with a first of three ECG lead positions which constitute an Eindoven's triangle on the user's body;

a second conductive electrode coupled to the electronic circuitry and adapted to facilitate continuous electrical contact with the user's body in a second Eindoven's triangle ECG lead position, the second electrode being separate from the apparatus casing; and a third conductive electrode coupled to the electronic circuitry and adapted to facilitate electrical contact with the user's body in a third Eindoven's triangle ECG lead position;

wherein the electronic circuitry includes a microprocessor which controls selective monitoring of the user's ECG data signals from one or more of six standard Eindoven's triangle ECG lead configurations when each of the three electrodes is in electrical contact with its associated ECG lead position on the user's body; and an electronic indicator means for the user to contact to generate a signal indicating that a cardiac event has occurred, wherein said electronic indicator means is a pushbutton switch which is disposed on a surface of the apparatus casing and electrically coupled to the microprocessor.

27. A portable, encased apparatus having electronic circuitry for continuously monitoring a user's electrocardiographic (ECG) data signals, said apparatus comprising:

a first conductive electrode coupled to the electronic circuitry and disposed on a surface of the apparatus casing so as to facilitate electrical contact with a first of three ECG lead positions which constitute an Eindoven's triangle on the user's body;

a second conductive electrode coupled to the electronic circuitry and adapted to facilitate continuous electrical contact with the user's body in a second Eindoven's triangle ECG lead position, the second electrode being separate from the apparatus casing;

a third conductive electrode coupled to the electronic circuitry and adapted to facilitate electrical contact with the user's body in a third Eindoven's triangle ECG lead position;

wherein the electronic circuitry includes a microprocessor which controls selective monitoring of the user's ECG data signals from one or more of six standard Eindoven's triangle ECG lead configurations when each of the three electrodes is in electrical contact with its associated ECG lead position on the user's body; and an electronic indicator means for the user to contact to generate a signal indicating that a cardiac event has occurred, wherein the microprocessor is programmable so as to permit a monitoring cycle to be selected in which ECG data signals are sequentially monitored from a first selected set of one or more of the six standard Eindoven's triangle ECG lead configurations until the user contacts said electronic indicator means, and after the user contacts said electronic indicator means, post-event ECG data signals are sequentially monitored from a second selected set of one or more of the six standard ECG lead configurations.

28. The apparatus of claim 27, wherein the electronic circuitry further comprises:

a power source;

circuit means coupled to the power source and the electrodes for receiving the user's analog ECG signals from one or more of six standard Eindoven's triangle lead configurations and for converting such signals into digitized format; and memory for receiving and storing the digitized ECG data;

wherein said microprocessor further controls storage of the digitized ECG data into the memory such that digitized ECG data is continuously stored, with new data being cyclically recorded over older data when the memory becomes full, until the user contacts said electronic indicator means, and after the user contacts said electronic indicator means, a predetermined quantity of the most recently stored ECG data is retained in the memory and post-event ECG data is stored in the remainder of the memory.

29. A portable, encased apparatus having electronic circuitry for continuously monitoring a user's electrocardiographic (ECG) data signals, said apparatus comprising:

a first conductive electrode coupled to the electronic circuitry and disposed on a surface of the apparatus casing so as to facilitate electrical contact with a first of three ECG lead positions which constitute an Eindoven's triangle on the user's body;

a second conductive electrode coupled to the electronic circuitry and adapted to facilitate continuous electrical contact with the user's body in a second Eindoven's triangle ECG lead position, the second electrode being separate from the apparatus casing; and a third conductive electrode coupled to the electronic circuitry and adapted to facilitate electrical contact with the user's body in a third Eindoven's triangle ECG lead position;

said electronic circuitry including circuit means coupled to the electrodes for receiving the user's analog ECG signals from one or more of six standard Eindoven's triangle lead configurations and for converting such signals into digitized format, said circuit means including a resistance summing network which comprises:

three input lines, each of which is coupled to a different one of the three conductive electrodes;

six resistors of equal impedance; and six output lines, of which three are each connected directly to a different one of the three input lines, and of which the other three are each connected via a pair of resistors to a different pair of the three input lines.

30. A portable, encased apparatus having electronic circuitry for continuously monitoring a user's electrocardiographic (ECG) data signals, said apparatus comprising:

a first conductive electrode coupled to the electronic circuitry and disposed on a surface of the apparatus casing so as to facilitate electrical contact with a first of three ECG lead positions which constitute an Eindoven's triangle on the user's body;

a second conductive electrode coupled to the electronic circuitry and adapted to facilitate continuous electrical contact with the user's body in a second Eindoven's triangle ECG lead position, the second electrode being separate from the apparatus casing; and a third conductive electrode coupled to the electronic circuitry and adapted to facilitate electrical contact with the user's body in a third Eindoven's triangle ECG lead position;

said electronic circuitry including a microprocessor which controls selective monitoring of the user's ECG data signals from one or more of six standard Eindoven's triangle ECG lead configurations when each of the three electrodes is in electrical contact with its associated ECG lead position on the user's body;

a power source;

circuit means coupled to the power source and the electrodes for receiving the user's analog ECG signals and for converting such signals into digitized format;

memory for receiving and storing the digitized ECG data, wherein said microprocessor further controls storage of the digitized ECG data into the memory; and an output which is coupled to the memory and adapted for transmission of the digitized ECG data to an external receiver, wherein the microprocessor, upon command of the user, controls the transmission of the digitized data from the memory to the external receiver via the output, wherein the microprocessor transmits the digitized data stored in the memory to the output in burst mode, thereby minimizing power consumption.

31. A portable, encased apparatus having electronic circuitry for continuously monitoring a user's electrocardiographic (ECG) data signals, said apparatus comprising:
- a first conductive electrode coupled to the electronic circuitry and disposed on a surface of the apparatus casing so as to facilitate electrical contact with a first of three ECG lead positions which constitute an Eindoven's triangle on the user's body;
- a second conductive electrode coupled to the electronic circuitry and adapted to facilitate continuous electrical contact with the user's body in a second Eindoven's triangle ECG lead position, the second electrode being separate from the apparatus casing; and
- a third conductive electrode coupled to the electronic circuitry and adapted to facilitate electrical contact with the user's body in a third Eindoven's triangle ECG lead position;
- said electronic circuitry including
  - a microprocessor which controls selective monitoring of the user's ECG data signals from one or more of six standard Eindoven's triangle ECG lead configurations when each of the three electrodes is in electrical contact with its associated ECG lead position on the user's body;
  - a power source;
  - circuit means coupled to the power source and the electrodes for receiving the user's analog ECG signals from one or more of six standard Eindoven's triangle lead configurations and for converting such signals into digitized format; and
  - a first in/first out ring memory for receiving and storing the digitized ECG data, wherein said microprocessor further controls storage of the digitized ECG data into the memory.

32. A portable, encased apparatus having electronic circuitry for continuously monitoring a user's electrocardiographic (ECG) data signals, said apparatus comprising:
- a first conductive electrode coupled to the electronic circuitry and disposed on a surface of the apparatus casing so as to facilitate electrical contact with a first of three ECG lead positions which constitute an Eindoven's triangle on the user's body;
- a second conductive electrode coupled to the electronic circuitry and adapted to facilitate continuous electrical contact with the user's body in a second Eindoven's triangle ECG lead position, the second electrode being separate from the apparatus casing; and
- a third conductive electrode coupled to the electronic circuitry and adapted to facilitate electrical contact with the user's body in a third Eindoven's triangle ECG lead position;
- wherein the electronic circuitry includes a microprocessor which controls selective monitoring of the user's ECG data signals from one or more of six standard Eindoven's triangle ECG lead configurations when each of the three electrodes is in electrical contact with its associated ECG lead position on the user's body; and
- an electrode, which is disposed on a surface of the apparatus casing and electrically coupled to the microprocessor, for the user to contact to generate a signal indicating that a cardiac event has occurred.

* * * * *